US00PP32267P2

(12) United States Plant Patent
Caster et al.

(10) Patent No.: US PP32,267 P2
(45) Date of Patent: Oct. 6, 2020

(54) BLUEBERRY PLANT VARIETY NAMED 'DRISBLUETWENTYONE'

(50) Latin Name: ***Vaccinium corymbosum* L.**
Varietal Denomination: DrisBlueTwentyOne

(71) Applicant: Driscoll's, Inc., Watsonville, CA (US)

(72) Inventors: Brian K. Caster, Watsonville, CA (US); Jennifer K. Izzo, Watsonville, CA (US)

(73) Assignee: Driscoll's, Inc., Watsonville, CA (US)

( * ) Notice: Subject to any disclaimer, the term of this patent is extended or adjusted under 35 U.S.C. 154(b) by 0 days.

(21) Appl. No.: 16/602,840

(22) Filed: Dec. 10, 2019

(51) Int. Cl.
*A01H 5/08* (2018.01)
*A01H 6/36* (2018.01)

(52) U.S. Cl.
USPC ..... Plt./157

(58) Field of Classification Search
USPC ..... Plt./157
See application file for complete search history.

(56) References Cited

U.S. PATENT DOCUMENTS

| | | | |
|---|---|---|---|
| PP6,699 | P | 3/1989 | Wood |
| PP11,807 | P2 | 3/2001 | Lyrene |
| PP12,783 | P2 | 7/2002 | Lyrene |
| PP15,146 | P3 | 9/2004 | Hancock |
| PP20,436 | P2 | 10/2009 | Caster et al. |
| PP20,449 | P2 | 11/2009 | Caster et al. |
| PP20,488 | P2 | 11/2009 | Caster et al. |
| PP24,407 | P3 | 4/2014 | Caster et al. |
| PP24,489 | P3 | 5/2014 | Caster et al. |
| PP24,568 | P3 | 6/2014 | Caster et al. |
| PP24,569 | P3 | 6/2014 | Caster et al. |
| PP24,605 | P3 | 7/2014 | Caster et al. |
| PP26,287 | P3 | 1/2016 | Caster et al. |
| PP26,451 | P3 | 3/2016 | Caster et al. |
| PP26,537 | P3 | 3/2016 | Caster et al. |
| PP26,643 | P3 | 4/2016 | Caster et al. |
| PP26,748 | P3 | 5/2016 | Caster et al. |
| PP27,622 | P3 | 1/2017 | Caster et al. |
| PP28,933 | P2 | 2/2018 | Caster et al. |

OTHER PUBLICATIONS

Caster et al., Unpublished U.S. Appl. No. 16/350,012, filed Sep. 12, 2018, titled "Blueberry Plant Variety Named 'DrisBlueEighteen'".
Caster et al., Unpublished U.S. Appl. No. 16/350,021, filed Sep. 13, 2018, titled "Blueberry Plant Variety Named 'DrisBlueSeventeen'".
Caster et al. "Unpublished U.S. Appl. No. 16/501,199, filed Mar. 5, 2019, titled "Blueberry Plant Variety Named 'DrisBlueTwenty'"".
Mowrey et al., Unpublished U.S. Appl. No. 16/350,020, filed Sep. 13, 2018, titled "Blueberry Plant Variety Named 'DrisBlueSixteen'".
Mowrey et al., Unpublished U.S. Appl. No. 16/350,226, filed Oct. 16, 2018, titled "Blueberry Plant Variety Named 'DrisBlueNineteen'".

*Primary Examiner* — Annette H Para
(74) *Attorney, Agent, or Firm* — Morrison & Foerster LLP

(57) ABSTRACT

A new and distinct variety of blueberry plant named 'DrisBlueTwentyOne', particularly selected for productivity, medium to large, firm, sweet-flavored fruit, and a mid-range chill hour requirement suitable for production in latitudes ranging from 30 to 40 degrees, is disclosed.

6 Drawing Sheets

Latin name:
Botanical classification: *Vaccinium corymbosum* L.
Varietal denomination: The varietal denomination of the claimed variety of blueberry plant is 'DrisBlueTwentyOne'.

BACKGROUND OF THE INVENTION

Blueberry plants are perennial flowering plants with indigo-colored berries from the section *Cyanococcus* within the genus *Vaccinium*. Many commercially sold species with English common names, including blueberry, are currently classified in section *Cyanococcus* of the genus *Vaccinium* and come predominantly from North America. Many North American native species of blueberries are grown commercially in the Southern Hemisphere in Australia, New Zealand, and South American nations.

*Vaccinium corymbosum*, the northern highbush blueberry, is a North American species of blueberry which has become a food crop of significant economic importance. It is native to eastern Canada and the eastern and southern United States, from Ontario east to Nova Scotia and south as far as Florida and eastern Texas. It has been naturalized in Europe, Japan, New Zealand, and the Pacific Northwest of North America. Other common names include blue huckleberry, tall huckleberry, swamp huckleberry, high blueberry, and swamp blueberry.

Blueberries are usually erect, prostrate shrubs that can vary in size from approximately four inches to approximately 13 feet in height. In the commercial production of blueberries, the smaller species are known as "lowbush blueberries", while the larger species are known as "highbush blueberries".

Blueberry bushes typically bear fruit in the middle of the growing season. However, fruiting times can be affected by local conditions such as altitude and latitude. As such, peak crop can vary from May to August in the northern hemisphere, depending upon these conditions.

Blueberries are a popular fruit that is typically consumed as fresh fruit, individually quick frozen (IQF) fruit, or in prepared foods, such as purées, juices, jellies, jams, baked goods, snack foods, and cereals.

Blueberry is an important and valuable fruit crop. Accordingly, there is a need for new varieties of blueberry plant. In particular, there is a need for improved varieties of blueberry plant that are stable, high yielding, and agronomically sound.

SUMMARY OF THE INVENTION

In order to meet these needs, the present invention is directed to an improved variety of blueberry plant. In particular, the invention relates to a new and distinct variety of blueberry plant (*Vaccinium corymbosum* L.), which has been denominated as 'DrisBlueTwentyOne'.

Blueberry plant variety 'DrisBlueTwentyOne' was discovered in Santa Cruz County, Calif. in September of 2006 and originated from a cross between the proprietary female parent blueberry plant '136D 2' (unpatented) and the proprietary male parent blueberry plant '181C 1' (unpatented). The original seedling of the new variety was first asexually propagated via softwood cuttings in Monterey County, Calif. in 2008.

'DrisBlueTwentyOne' was subsequently asexually propagated via softwood cuttings and underwent further testing in Santa Cruz, Calif. for eleven years (2008 to 2019). The present blueberry variety has been found to be stable and reproduce true to type through successive asexual propagations via softwood cuttings.

'DrisBlueTwentyOne' exhibits the following distinguishing characteristics when grown under normal horticultural practices in Santa Cruz, Calif.:

1. Elliptic leaf shape;
2. Light intensity of green color of unripe fruit color; and
3. Dark blue color of mature fruit after removal of bloom.

'DrisBlueTwentyOne' was selected for its productivity, medium to large, firm, sweet-flavored fruit, and a mid-range chill hour requirement suitable for production in latitudes ranging from 30 to 40 degrees.

BRIEF DESCRIPTION OF THE DRAWINGS

This new blueberry plant variety is illustrated by the accompanying photograph. The colors shown are as true as can be reasonably obtained by conventional photographic procedures. The photograph is of plants that are eight years old, unless otherwise specified.

DETAILED BOTANICAL DESCRIPTION

Figure 1:
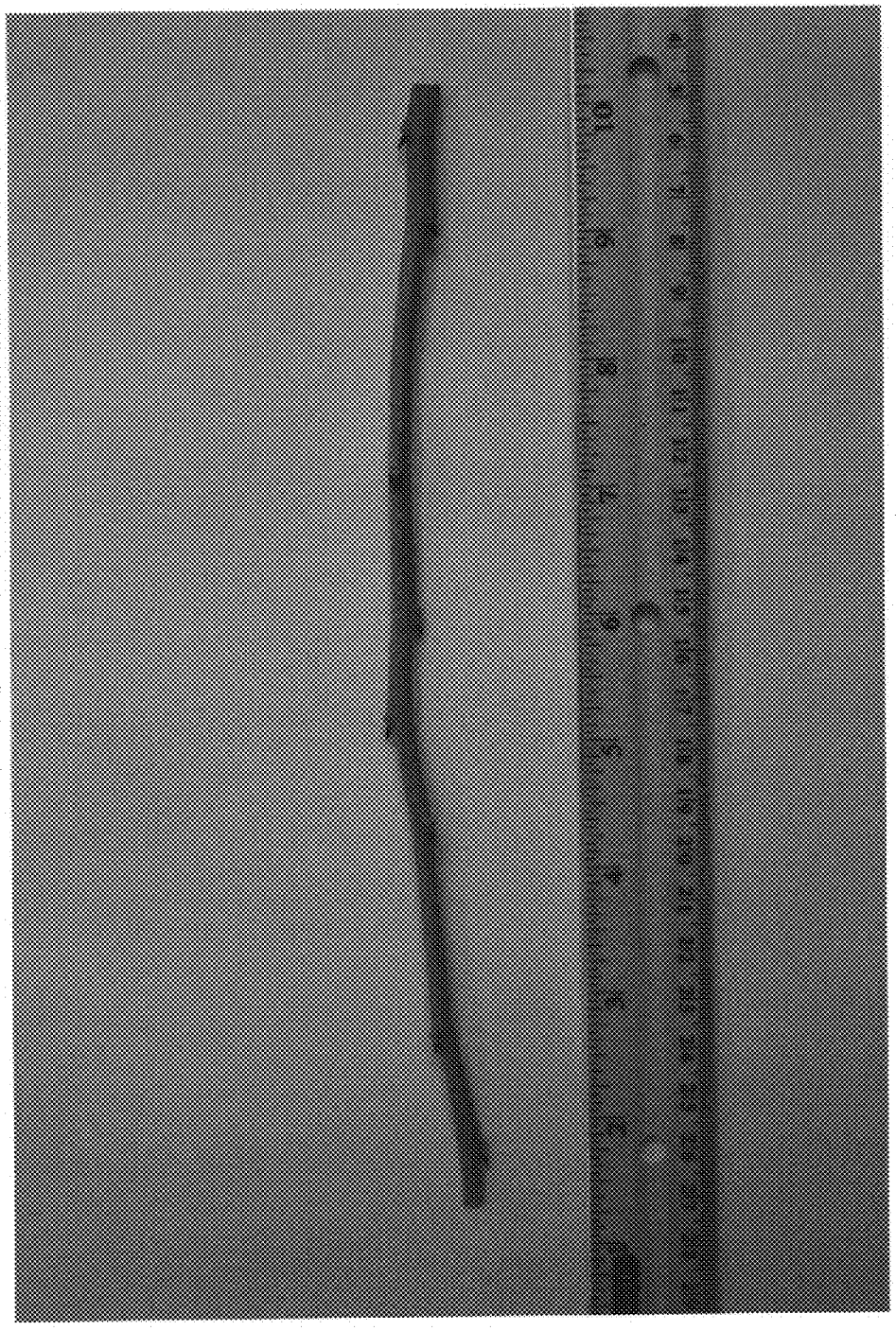
FIG. 1 illustrates a section of a cane of variety 'DrisBlueTwentyOne'.
Figure 2:
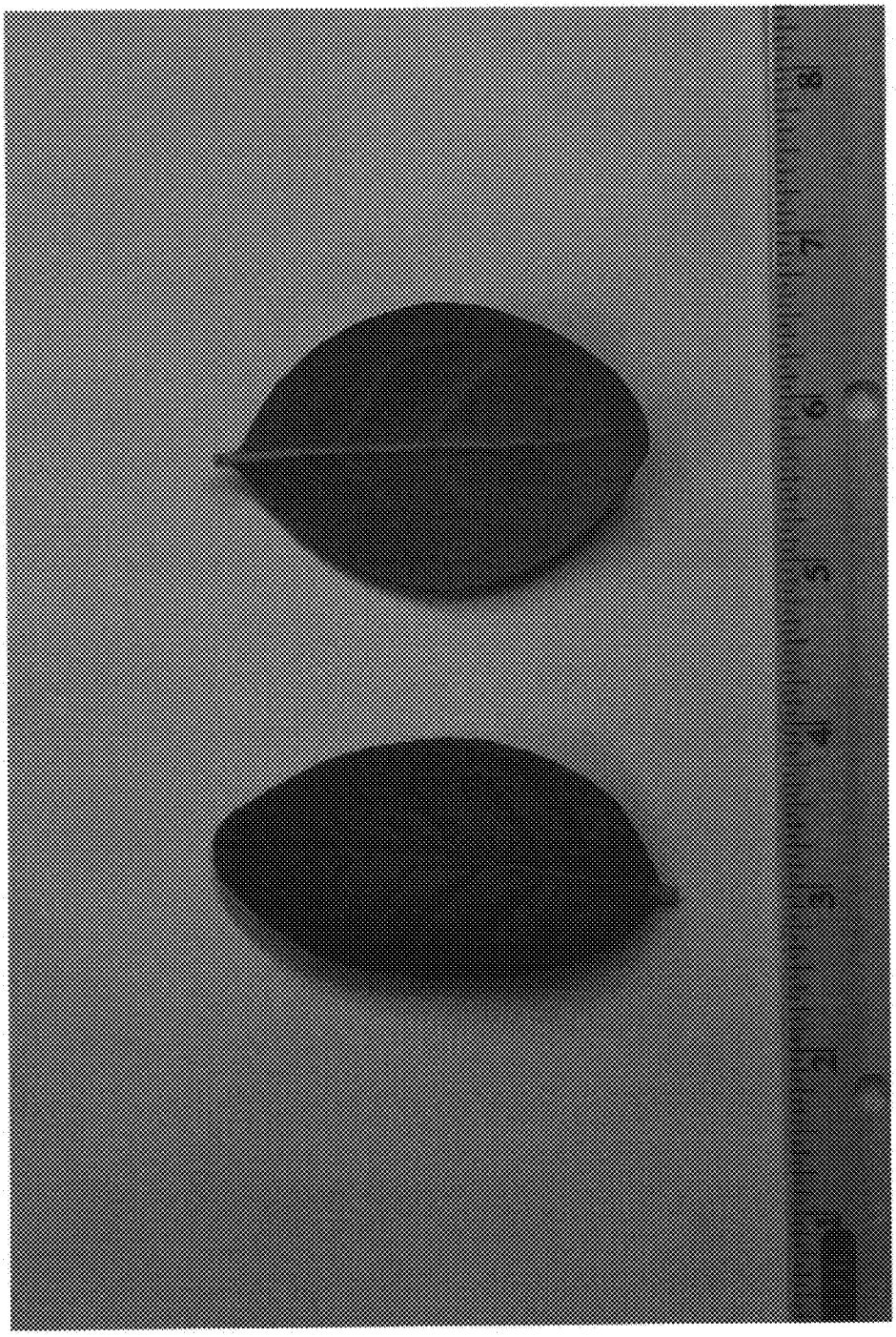
FIG. 2 illustrates leaves of variety 'DrisBlueTwentyOne'. The upper leaf surface is shown on the left side and the lower leaf surface is shown on the right side.
Figure 3:
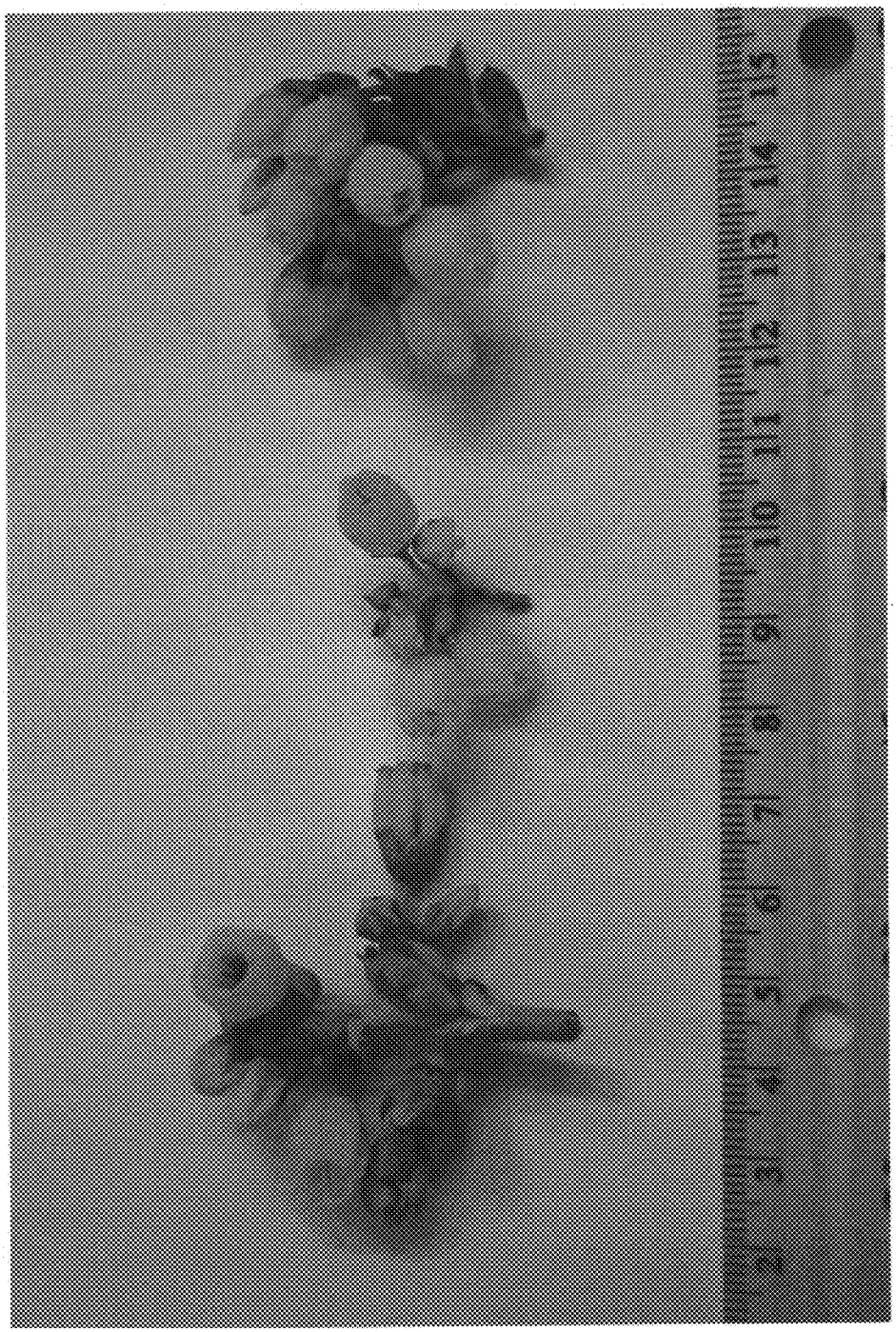
FIG. 3 illustrates clusters of flowers of variety 'DrisBlueTwentyOne'.
Figure 4:
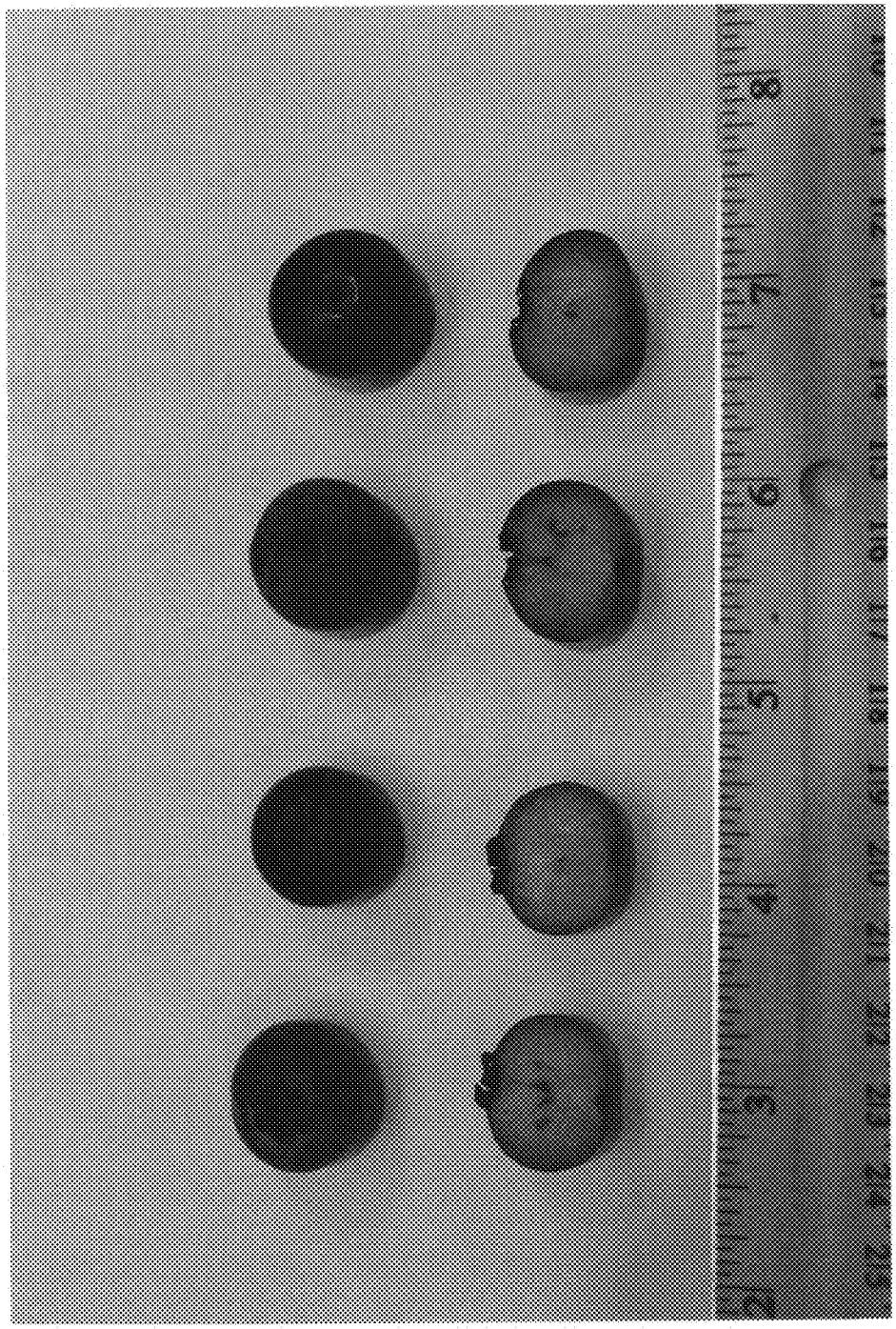
FIG. 4 illustrates whole fruit (top row) and longitudinal sections (bottom row) of the fruit of variety 'DrisBlueTwentyOne'. On the top row, counting from left, the first and second fruit show the top view (calyx basin) of the whole fruit, and the third and fourth fruit show the bottom view (fruit-pedicel junction) of the whole fruit, and the second and fourth fruit have the bloom removed.
Figure 5:
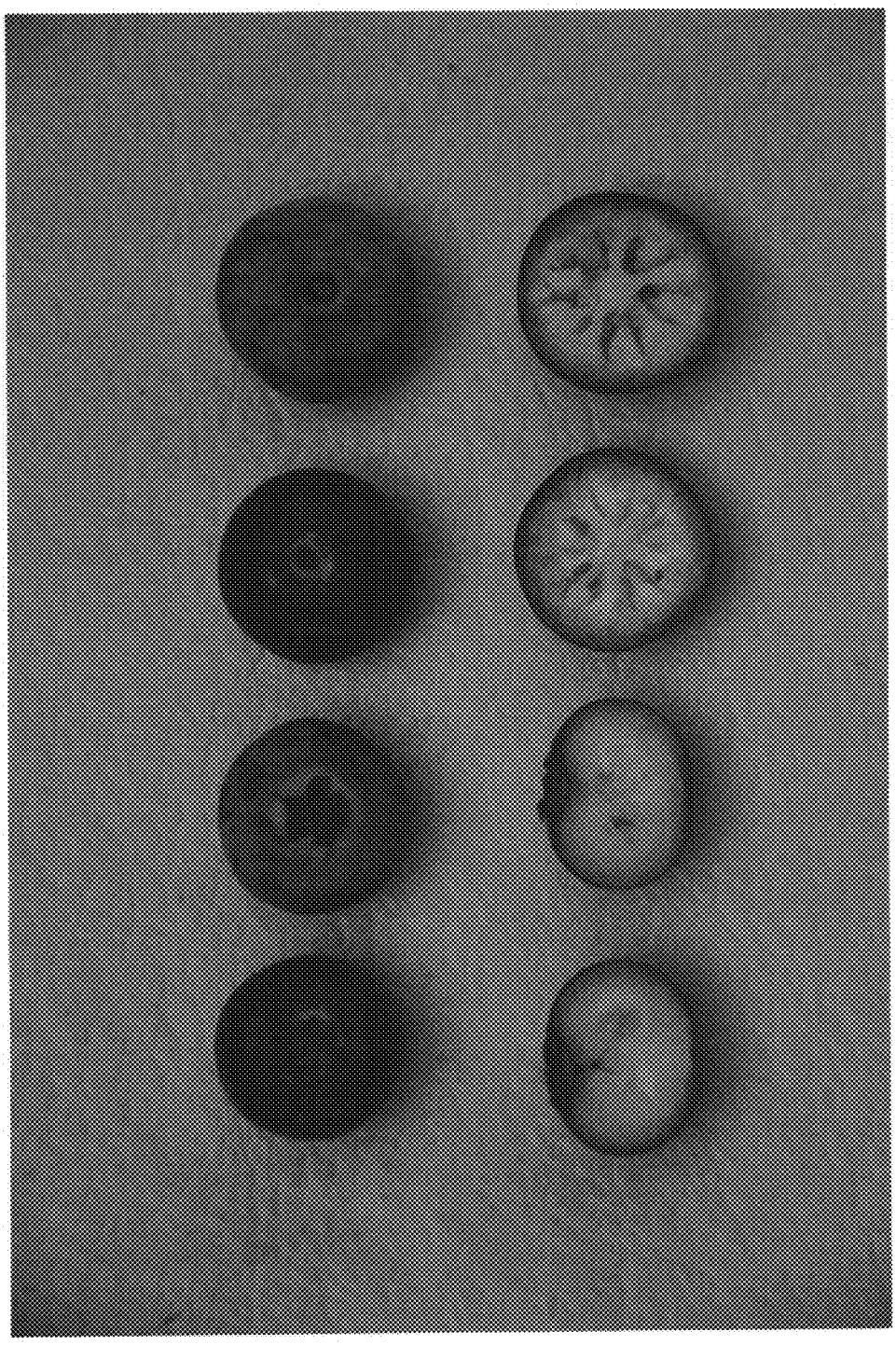
FIG. 5 illustrates whole fruit (top row), cross-sections (bottom row, right two fruit) and longitudinal sections (bottom row, left two fruit) of the fruit of variety 'DrisBlueTwentyOne'. On the top row, counting from left, the first and second fruit show the top view (calyx basin) of the whole fruit, the third and fourth fruit show the bottom view (fruit-pedicel junction) of the whole fruit, and the first and third fruit have the bloom removed.
Figure 6:
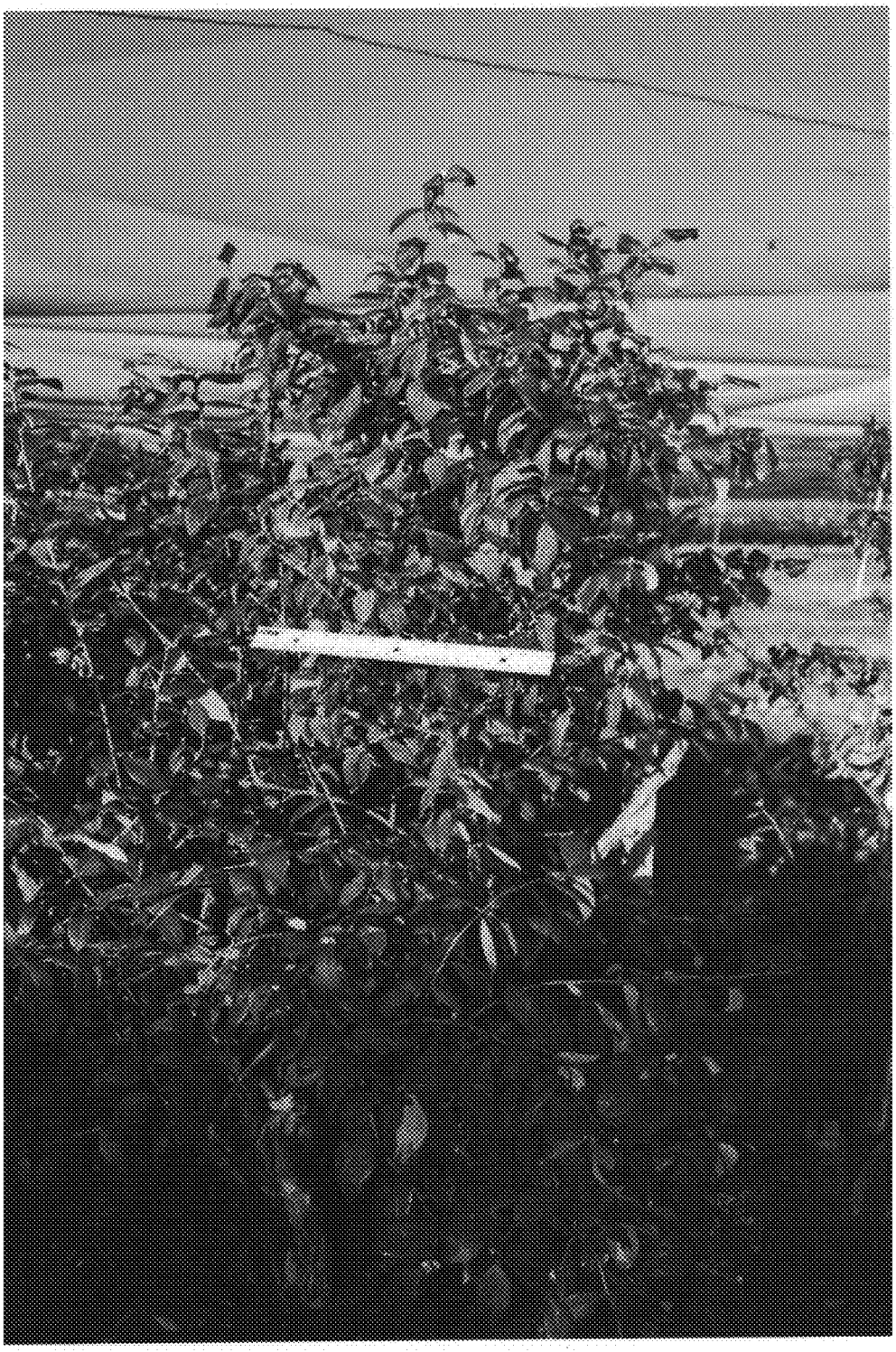
FIG. 6 illustrates a plant of variety 'DrisBlueTwentyOne'.

The following description sets forth the distinctive characteristics of 'DrisBlueTwentyOne'. The data which define these characteristics is based on observations taken in Santa Cruz, Calif. from 2008 to 2019. This description is in accordance with UPOV terminology. Color designations, color descriptions, and other phenotypical descriptions may deviate from the stated values and descriptions depending upon variation in environmental, seasonal, climatic and cultural conditions. 'DrisBlueTwentyOne' has not been observed under all possible environmental conditions. The botanical description of 'DrisBlueTwentyOne' was taken from eight-year-old plants, unless noted otherwise. The indicated values represent averages calculated from measurements of several plants. Color references are primarily to The R.H.S. Colour Chart of The Royal Horticultural Society of London (R.H.S.) (2007 edition). Descriptive terminology follows the *Plant Identification Terminology, An Illustrated Glossary,* 2$^{nd}$ edition by James G. Harris and Melinda Woolf Harris, unless where otherwise defined.

Classification:

*Family*.—Ericaceae.
*Botanical*.—*Vaccinium corymbosum* L.
*Common name*.—Blueberry.
*Variety name*.—'DrisBlueTwentyOne'.

Parentage:

*Female parent*.—The proprietary blueberry plant '136D 2' (unpatented).
*Male parent*.—The proprietary blueberry plant '181C 1' (unpatented).

Plant:

*Height*.—172.2 cm.
*Width*.—202.2 cm.
*Length/width ratio*.—0.9.
*Growth habit*.—Semi-upright.
*One-year-old canes* (*young canes*).—Length: 45 cm. Diameter at the base: 8 mm. Diameter at the tip: 2 mm. Internode length on the upper half: 13.0 mm. Color: RHS 145A (Yellow-green). Texture: Smooth.
*Five-year-old canes* (*mature canes*).—Length: 157 cm. Diameter at the base: 28 mm. Diameter at the tip: 2 mm. Color: RHS 199D (Grey-brown). Texture: Rough.

Leaves:

*Length*.—56.6 mm.
*Width*.—27.8 mm.
*Length/width ratio*.—2.0.
*Internode length*.—12.98 mm.
*Shape*.—Elliptic.
*Margin*.—Entire.
*Color on upper side*.—RHS 133 (Dark green).
*Color of underside*.—RHS 148C (Yellow-green).
*Arrangement*.—Alternate.
*Venation*.—Reticulate.
*Apex shape*.—Acute.
*Base shape*.—Cuneate.
*Trichomes on upper side*.—Glabrous (Absent).
*Sheath*.—Absent.
*Petiole*.—Length: 3.0 mm. Diameter: 1.21 mm. Color: RHS 145B (Yellow-green).

Flowers:

*Inflorescence length* (*excluding peduncle*).—Medium.

*Flower length* (*excluding peduncle*).—11.58 mm.

*Flower diameter.*—6.02 mm.

*Flower length/width ratio.*—1.9.

*Flower color.*—RHS 157A (Green-white).

*Fragrance.*—Medium.

*Flower bud.*—Length: 6 mm. Width: 4 mm. Number of flowers per bud: 7. Color on immature buds: RHS 183A (Dark red). Color on mature buds: RHS 64B (Strong purplish red). Anthocyanin color: RHS 166B (Moderate reddish brown).

*Pedicel.*—Length: 3.20 mm. Diameter: 0.84 mm. Color: RHS 143C (Green).

*Corolla.*—Shape: Urceolate. Anthocyanin coloration of corolla tube: Very weak, on unopened flowers only. Anthocyanin color of corolla tube: RHS 58B (Red-purple). Ridges on corolla tube: Present. Petal width (ridge to ridge): 3.73 mm. Diameter of corolla aperture: 2.69 mm.

*Reproductive organs.*—Style length (including stigma): 8.49 mm. Style color: RHS 145A (Yellow-green). Ovary color: RHS 191B (Greyed-green). Anther color: RHS N172D (Greyed-orange).

*Flowering interval on one-year shoot.*—March-April.

Fruit:

*Length.*—11.45 mm.

*Diameter.*—11.21 mm.

*Length/width ratio.*—1.0.

*Shape in longitudinal section.*—Round.

*Attitude of sepals.*—Semi-erect.

*Type of sepals.*—Incurving.

*Calyx basin.*—Diameter: 5.46 mm. Depth: 3.31 mm. Diameter/depth ratio: 1.6.

*Number of berries per cluster.*—2.90.

*Peduncle length.*—14.70 mm.

*Diameter of pedicel.*—0.80 mm.

*Seed.*—Length: 1.28 mm. Width: 0.72 mm. Length/width ratio: 1.8. Seed color: RHS 163A (Greyed-orange).

*Color of unripe fruit.*—RHS 145D (Yellow-green).

*Color of skin without bloom on immature* (*maturing, not green*) *fruit.*—RHS 59A (Red-purple).

*Color of fruit without bloom on mature fruit.*—RHS 99A (Dark-blue).

*Color of skin with bloom on mature fruit.*—RHS 97A (Violet-blue).

*Flesh color.*—RHS 145B (Yellow-green).

*Fruit firmness.*—Firm.

*Fruit sweetness.*—Low.

*Fruit acidity.*—Low.

*Fruiting type.*—On one-year-old shoots only.

*Ripening interval on one-year-old shoot.*—Mid-June to mid-August.

*Yield.*—8,000 kg to 12,000 kg of fruit per hectare per season from 60-month old plants when grown at Watsonville, Calif.

Resistance to abiotic stress, pests, and diseases:

*Heat.*—Moderately susceptible.

*Spotted-wing drosophila* (*Drosophila suzukii*).—Moderately susceptible.

*Botrytis fruit rot* (*Botrytis cinerea*).—Moderately susceptible.

*Botryosphaeria stem blight.*—Moderately susceptible.

*Phomopsis stem blight.*—Moderately susceptible.

COMPARISONS TO PARENTAL AND COMMERCIAL BLUEBERRY VARIETIES

'DrisBlueTwentyOne' differs from the proprietary female parent '136D 2' (unpatented) in that 'DrisBlueTwentyOne' has higher yield in a concentrated ripening period when compared to '136D 2'.

'DrisBlueTwentyOne' differs from the proprietary male parent '181C 1' (unpatented) in that fruit of 'DrisBlueTwentyOne' are larger in size than fruit of '181C 1'.

'DrisBlueTwentyOne' differs from commercial blueberry plant variety 'DrisBlueOne' (U.S. Plant Pat. No. 20,449) in that flowers of 'DrisBlueTwentyOne' have a medium size of corolla tube, whereas flowers of 'DrisBlueOne' have a large size of corolla tube. Moreover, unripe fruit of 'DrisBlueTwentyOne' have a light intensity of green color, whereas unripe fruit of 'DrisBlueOne' have a medium intensity of green color. Further, mature fruit of 'DrisBlueTwentyOne' have a dark blue color of skin after removal of bloom, whereas mature fruit of 'DrisBlueOne' have a medium blue color of skin after removal of bloom. Additionally, fruit of 'DrisBlueTwentyOne' have a low sweetness, whereas fruit of 'DrisBlueOne' have a medium sweetness.

'DrisBlueTwentyOne' differs from the commercial blueberry plant variety 'DrisBlueTwo' (U.S. Plant Pat. No. 20,488) in that one-year-old shoot of 'DrisBlueTwentyOne' has a green color, whereas on-year-old shoot of 'DrisBlueTwo' has a greyish red color. Moreover, leaves of 'DrisBlueTwentyOne' have an elliptic shape, whereas leaves of 'DrisBlueTwo' have an ovate shape. Further, leaves of 'DrisBlueTwentyOne' have an entire margin, whereas leaves of 'DrisBlueTwo' have a serrate margin. Additionally, unripe fruit of 'DrisBlueTwentyOne' have a light intensity of green color, whereas unripe fruit of 'DrisBlueTwo' have a dark intensity of green color.

What is claimed is:

1. A new and distinct variety of blueberry plant designated 'DrisBlueTwentyOne' as shown and described herein.

* * * * *